(12) United States Patent
Xu

(10) Patent No.: US 9,757,380 B2
(45) Date of Patent: Sep. 12, 2017

(54) METHODS FOR TREATING NEOPLASIA WITH COMBINATION OF CHEMOTHERAPEUTIC AGENTS AND RADIATION

(75) Inventor: Bo Xu, Hoover, AL (US)

(73) Assignee: Southern Research Institute, Birmingham, AL (US)

( * ) Notice: Subject to any disclaimer, the term of this patent is extended or adjusted under 35 U.S.C. 154(b) by 1148 days.

(21) Appl. No.: 12/102,237

(22) Filed: Apr. 14, 2008

(65) Prior Publication Data

US 2008/0262003 A1    Oct. 23, 2008

Related U.S. Application Data

(60) Provisional application No. 60/911,874, filed on Apr. 14, 2007.

(51) Int. Cl.
| | |
|---|---|
| *A61K 31/52* | (2006.01) |
| *A61K 31/355* | (2006.01) |
| *A61K 41/00* | (2006.01) |

(52) U.S. Cl.
CPC ............ *A61K 31/52* (2013.01); *A61K 31/355* (2013.01); *A61K 41/0038* (2013.01)

(58) Field of Classification Search
None
See application file for complete search history.

(56) References Cited

U.S. PATENT DOCUMENTS

| | | |
|---|---|---|
| 5,585,363 A | 12/1996 | Scanlon et al. |
| 2003/0229004 A1 | 12/2003 | Zarling et al. |
| 2005/0272755 A1 | 12/2005 | Denis et al. |

FOREIGN PATENT DOCUMENTS

| | | |
|---|---|---|
| CN | 1887257 A | 1/2007 |
| WO | WO-9220347 A1 | 11/1992 |

(Continued)

OTHER PUBLICATIONS

Cunningham et al. Clofarabine administered weekly to adult patients with advanced solid tumors in a phase I dose-finding study. Journal of Clinical Oncology, 2004 ASCO Annual Meeting Proceedings, vol. 22, No. 14S (Jul. 15 Supplement), 2004:3115.*

(Continued)

*Primary Examiner* — Anna Pagonakis
(74) *Attorney, Agent, or Firm* — POLSINELLI PC

(57) ABSTRACT

Methods for treating neoplasia with a chemotherapeutic agent and radiation are provided. Radiation therapies used in conduction with a compound described herein presents a synergistic effect in the treatment of cancers. A compound of formula (I):

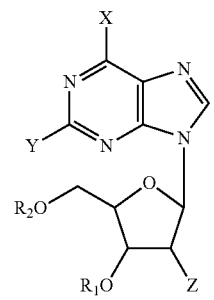

Formula (I)

wherein X, Y, Z, $R_1$ and $R_2$ are defined herein, sensitize cells making them more susceptible to radiation therapy.

7 Claims, 9 Drawing Sheets

(56) References Cited

FOREIGN PATENT DOCUMENTS

| WO | WO-2005094282 A2 | 10/2005 |
|---|---|---|
| WO | WO-2006040558 A1 | 4/2006 |
| WO | WO-2006048768 A2 | 5/2006 |

OTHER PUBLICATIONS

USC Center for Pancreatic and Biliary Diseases. 2002.*
Cheson et al. [Editor]. Nucleoside Analogs in Cancer Therapy, pp. 318-319.*
Vippagunta et al. Advanced Drug Delivery Reviews, 48, 2001, p. 18.*
Wolff et al. Burgers Medicinal Chemistry and Drug Discovery—Fifth Edition, New York: John Wiley & Songs, 1996, vol. 1, pp. 975-976.*
Dorwald F. Zaragoza. Side Reviews in Organic Synthesis: A guide to successful synthesis design, Weinheim: WILEY-VCH, Verlag, Gmbh & Co. KGaA, 2005, Preface.*
Jordan, V.C. Nature Reviews: Drug Discovery, 2, 2003, p. 205.*
Clofarabine (NDA 21-673). Oncologic Drug Advisory Committee Briefing Document, Dec. 1, 2004, meeting ILEX Products.*
Galmarini et al. Nucleoside analogues and nucleobases in cancer treatment. The Lancet. Oncology, vol. 3, Jul. 2002.*
International Search Report and Written Opinion issued in counterpart International Application No. PCT/US08/60214 mailed Jul. 14, 2008.
Cariveau Mickael et al., "Clofarabine Acts Synergistically With Ionizing Radiation In Vitro and In Vivo by Inhibiting the Repair of DNA Damage," Proceedings of the American Association for Cancer Research Annual Meeting, vol. 48, Apr. 14, 2007 , p. 1196, XP001539782.
Cariveau et al., "Clofarabine Acts as Radiosensitizer In Vitro and In Vivo by Interfering With DNA Damage Response," International Journal of Radiation: Oncology Biology Physics, Pergamon Press, USA LNKD—DOI: 10.1016/J. IJROBP.2007.09.012, vol. 70, No. 1, Nov. 26, 2007, pp. 213-220, XP022390610.
Bonate Peter L et al., "Discovery and Development of Clofarabine: A Nucleoside Analogue for Treating Cancer," Nature Reviews. Drug Discovery Oct. 2006 LNKD-PUBMED: 17016426, vol. 5, No. 10, Oct. 2006, pp. 855-863, XP009135419.
Supplemental European Search Report and Annex dated Jun. 28, 2010 in corresponding European Application No. EP08745749.
Gandhi V. et al., "Clinical and Pharmacokinetic Study of Clofarabine in Chronic Lymphocytic Leukemia: Strategy for Treatment", Cancer Therapy: Clinical, 2006, vol. 12, No. 13, pp. 4011-4017.
Office Action issued in Australian Application No. 2008240118 on Nov. 6, 2012.
Office Action issued in Mexican Application No. MX/a/2009/011104 on Jul. 30, 2013.
Office Action issued in New Zealand Application No. 580463 on Oct. 8, 2010.
English Translation of Office Action issued in Japanese Application No. 2010-503,268 on Mar. 19, 2013.
English Translation of First Office Action issued in Chinese Application No. 200880015796.0 on May 3, 2012.
Office Action issued in Eurasian Application No. 200970949/28 on Apr. 22, 2011.
Office Action issued in Canadian Application No. 2,683,637 on Aug. 12, 2011.
European Search Opinion and Supplementary European Search Report issued in European Application No. 08 745 749.5.

* cited by examiner

Antitumor Activity of Clofarabine in SKOV-3 Cells

Antitumor Activity of Clofarabine in IGROV-1 Cells

METHODS FOR TREATING NEOPLASIA WITH COMBINATION OF CHEMOTHERAPEUTIC AGENTS AND RADIATION

RELATION APPLICATION

This nonprovisional application claims priority under 35 U.S.C. §119(e) to U.S. Provisional Application No(s). 60/911,874 filed on Apr. 14, 2007, the entire contents of which are hereby incorporated by reference.

TECHNICAL FIELD

The present disclosure relates generally to the fields of molecular biology, radiation oncology and cancer therapy. More specifically, the present disclosure relates to the finding that a combination of certain molecular chemotherapy and radiation treatment enhances therapeutic effects against cancer.

BACKGROUND

Cancer is a worldwide problem that afflicts millions of people each year. As such, finding methods for its treatment is of vital interest. Both chemotherapy and radiation are used in the treatment of cancer. Chemotherapy refers to the use of chemical compounds or drugs in the treatment of disease, though the term chemotherapy is most often associated with the treatment of cancer. Cancer chemotherapeutic agents are also commonly referred to as antineoplastic agents. The severe side effects experienced with the majority of cancer chemotherapeutics are a result of the non-specific nature of these drugs, which do not distinguish between healthy and cancerous cells, and instead destroy both. The cell cycle specific drugs attempt to lessen these effects, targeting phases of the cell cycle involved in cell replication and division. These drugs do not, however, distinguish between cancerous cells and healthy cells which are undergoing normal cell division. The cells most at risk from these types of chemotherapy are those which undergo cell division often, including blood cells, hair follicle cells, and cells of the reproductive and digestive tracts.

The most common side effects of chemotherapeutic agents are nausea and vomiting. A large proportion of individuals also suffer from myelosuppression, or suppression of the bone marrow, which produces red blood cells, white blood cells and platelets. These and other side effects are also exacerbated by the suppression of the immune system concomitant with the destruction and lack of production of white blood cells, and associated risk of opportunistic infection. Other side effects common to a wide range of chemotherapeutic agents include hair loss (alopecia), appetite loss, weight loss, taste changes, stomatitis and esophagitis (inflammation and sores), constipation, diarrhea, fatigue, heart damage, nervous system changes, lung damage, reproductive tissue damage, liver damage, kidney and urinary system damage.

Radiation is another commonly used treatment for cancer, used in approximately 60% of treatment regimens. Often combined with chemotherapy and/or surgery, radiation therapy encompasses both local and total body administration as well as a number of new advances, including radioimmunotherapy. The cytotoxic effect of radiation on neoplastic cells arises from the ability of radiation to cause a break in one or both strands of the DNA molecule inside the cells. Cells in all phases of the cell cycle are susceptible to this effect. However, the DNA damage is more likely to be lethal in cancerous cells because they are less capable of repairing DNA damage. Healthy cells, with functioning cell cycle checkpoint proteins and repair enzymes are far more likely to be able to repair the radiation damage and function normally after treatment.

The side effects of radiation are similar to those of chemotherapy and arise for the same reason, the damage of healthy tissue. Radiation is usually more localized than chemotherapy, but treatment is still accompanied by damage to previously healthy tissue. Many of the side effects are unpleasant, and radiation also shares with chemotherapy the disadvantage of being mutagenic, carcinogenic and teratogenic in its own right. While normal cells usually begin to recover from treatment within two hours of treatment, mutations may be induced in the genes of the healthy cells. These risks are elevated in certain tissues, such as those in the reproductive system. Also, it has been found that different people tolerate radiation differently. Doses that may not lead to new cancers in one individual may in fact spawn additional cancers in another individual. This could be due to pre-existing mutations in cell cycle checkpoint proteins or repair enzymes, but current practice would not be able to predict at what dose a particular individual is at risk. Common side effects of radiation include bladder irritation, fatigue, diarrhea, low blood counts, mouth irritation, taste alteration, loss of appetite, alopecia, skin irritation, change in pulmonary function, enteritis, sleep disorders, and others.

Chemotherapy treatment and a radiation therapy may be combined in the treatment of cancers but often the patient suffers increased risk due to the cumulative side-effects and toxicity of each treatment. A synergistic effect allows for less exposure to toxic chemotherapeutic agents and radiation therapy, thereby reducing side-effects, while achieving an improved beneficial result.

SUMMARY

The disclosure relates generally to methods for enhancing the radiosensitivity of cells and also to methods of treating cancers with a compound or compounds of the present disclosure in conjunction with radiotherapy.

One embodiment of the present disclosure is drawn to a method of conferring radiation sensitivity on a tumor cell comprising administering to said cell a compound of formula (I):

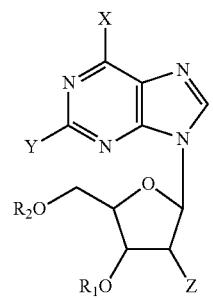

Formula (I)

wherein

X and Y are the same or different and are hydrogen, halogen, $OR_3$, $SR_3$, $NR_3R_4$ or NHacyl;

Z is a halogen or $CF_3$.

$R_3$ and $R_4$ being the same or different and being hydrogen, a lower alkyl of 1 to 7 carbon atoms, an aralkyl compound selected from the group consisting of benzyl, benzyhydryl or methoxybenzyl, or an aryl compound selected from the group consisting of phenyl, chlorophenyl, toluoyl, methoxyphenyl and naphthyl;

NHacyl being alkanoyl or aroyl amide, alkanoyl being an alkyl carbonyl radical in which alkyl is a straight or branched chain saturated or unsaturated hydrocarbon radical having from 1 to 20 carbon atoms; and $R_1$ and $R_2$ are the same or different and are hydrogen, acyl or aroyl, acyl being an alkanoyl group of 1 to 20 carbon atoms and aroyl being benzoyl or naphthoyl; and salts, solvates, derivatives and prodrugs thereof.

Another embodiment of the present disclosure is drawn to a method of conferring radiation sensitivity on a tumor cell comprising administering to said cell a compound of formula (I-a):

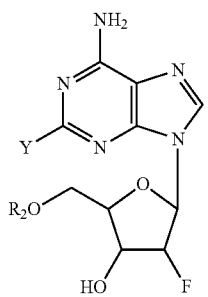

Formula (I-a)

wherein
Y is F, Cl, or Br;
$R_2$ is hydrogen or acyl; and salts, solvates, derivatives and prodrugs thereof.

Another embodiment is drawn to methods for enhancing radiosensitivity of cell populations comprising exposing said cell populations to a sensitizing amount of a compound of formula (I). Also provided herewith are methods for treating tumor growth comprising administering to a patient in need thereof a synergistic combination of radiation and a compound of formula (I). All methods provided herein may also further comprise administering compounds of formula (I) concurrently with radiation throughout the course of treatment. For instance, compounds of formula (I) may be administered daily for a period before, after, or throughout the course of radiation therapy. In one embodiment, a compound of formula (I) is administering after directing radiotherapy but close enough in time to exhibit a combinatorial or synergistic effect. Likewise, a compound of formula (I) may be administered before directing radiotherapy but close enough in time to exhibit a combinatorial or synergistic effect.

While not limiting the scope of the disclosure, cancers treatable by the methods disclosed herein include, but are not limited to a colon cancer, a colorectal cancer, a pancreatic cancer, a liver cancer, a soft tissue cancers, a brain cancer, a head-and-neck cancer, a gastrointestinal cancer, a breast cancer, an ovarian cancer, a lymphoma, a sarcoma, a melanoma cancer of the cervix or endometrium, a bladder cancer, a renal cancer, or an ocular cancer.

DETAILED DESCRIPTION OF THE DISCLOSURE

Figure 1:
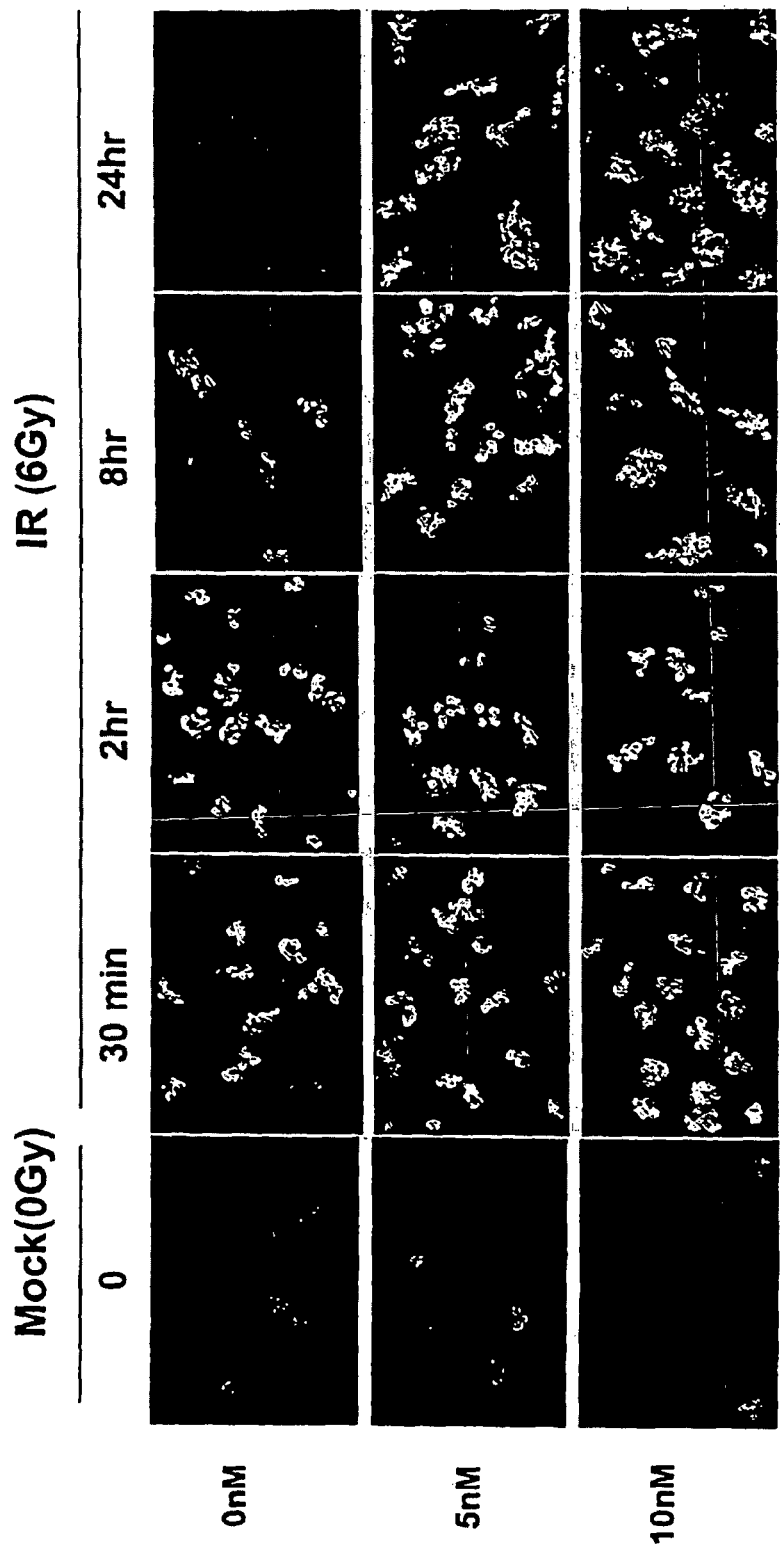
FIG. 1 is an immunofluorescence microscopy photograph showing the detection of radiation-induced γ-H2AX foci of cells treated with different concentrations of clofarabine.

The disclosure relates generally to methods of enhancing the radiosensitivity of cells and also to methods for treating cancers with a compound or compounds of the present disclosure in conjunction with radiotherapy.

As employed above and throughout the disclosure, the following terms, unless otherwise indicated, shall be understood to have the following meanings.

As used herein, the terms "neoplastic cells", "neoplasia", "tumor", "tumor cells", "cancer" and "cancer cells" are used interchangeably and refer to cells which exhibit relatively autonomous growth, so that they exhibit an aberrant growth phenotype characterized by a significant loss of control of cell proliferation. Neoplastic cells can be malignant or benign.

The terms "antineoplastic agent", "antineoplastic chemotherapeutic agent", "chemotherapeutic agent", "antineoplastic" and "chemotherapeutic" are used interchangeably and refer to chemical compounds or drugs which are used in the treatment of cancer e.g., to kill cancer cells and/or lessen the spread of the disease.

"Radiation therapy" is a term commonly used in the art to refer to multiple types of radiation therapy including internal and external radiation therapy, radioimmunotherapy, and the use of various types of radiation including X-rays, gamma rays, alpha particles, beta particles, photons, electrons, neutrons, radioisotopes, and other forms of ionizing radiation. As used herein, the terms "radiation therapy" and "radiation" are inclusive of all of these types of radiation therapy, unless otherwise specified.

The terms, "suppressing tumor growth", "treating tumor growth", and "treating cancer", and the like refer to reducing the rate of growth of a tumor, halting tumor growth completely, causing a regression in the size of an existing tumor, eradicating an existing tumor and/or preventing the occurrence of additional tumors upon treatment with the compositions, kits or methods of the present disclosure. "Suppressing" tumor growth indicates a growth state that is curtailed when compared to growth without administration of a compound disclosed herein in conjunction with radiation.

Tumor cell growth can be assessed by any means known in the art, including, but not limited to, measuring tumor size, determining whether tumor cells are proliferating using a 3H-thymidine incorporation assay, or counting tumor cells. "Suppressing" tumor cell growth means any or all of the following states: slowing, delaying, and stopping tumor growth, as well as tumor shrinkage.

"Delaying development" of a tumor means to defer, hinder, slow, retard, stabilize, and/or postpone development of the disease. This delay can be of varying lengths of time, depending on the history of the disease and/or individual being treated.

As used herein, "synergy" or "synergistic effect" when referring to combination administration of a compound of the present disclosure in conjunction with radiation means that the effect of the combination is more than additive when compared to administration of the compound(s) and radiation alone.

"A," "an" and "the" include plural references as well as singular references unless the context clearly dictates otherwise.

"Effective amount" refers to an amount of a compound as described herein that may be therapeutically effective to treat a disease or disorder associated with the instant disclosure. The precise amount of these compounds required will vary with the particular compounds or derivatives employed, the age and condition of the subject to be treated, and the nature and severity of the condition. However, the effective amount may be determined by one of ordinary skill in the art with only routine experimentation. An effective amount of radiation can be determined without undue experimentation by one of ordinary skill in the art. Radiation parameters, such as dosing amount and frequency are well-known in the art.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"Pharmaceutically acceptable salts" refer to derivatives of the disclosed compounds wherein the parent compound is modified by making acid or base salts thereof. The compounds of this disclosure form acid and base addition salts with a wide variety of organic and inorganic acids and bases and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

"Patient" refers to animals, including mammals, preferably humans.

"Metabolite" refers to any substance resulting from chemical changes involved in the processes of growth and repair in a living organism, including the anabolic and catabolic processes.

A "Prodrug" is a compound that is converted within the body into its active form that has a medical effect. Prodrugs may be useful when the active drug may be too toxic to administer systemically, the active drug is absorbed poorly by the digestive tract, or the body breaks down the active drug before it reaches its target. Methods of making prodrugs are disclosed in Hans Bundgaard, DESIGN OF PRODRUGS (Elsevier Science Publishers B.V. 1985), which is incorporated herein by reference in its entirety.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

The term "comprising" (and its grammatical variations) as used herein is used in the inclusive sense of "having" or "including" and not in the exclusive sense of "consisting only of" The term "consisting essentially of" as used herein is intended to refer to including that which is explicitly recited along with what does not materially affect the basic and novel characteristics of that recited or specified.

In the formulas described and claimed herein, it is intended that when any symbol appears more than once in a particular formula or substituent, its meaning in each instance is independent of the other.

One embodiment of the present disclosure is drawn to a method of potentiating radiotherapy treatment comprising administering to a patient in need thereof a therapeutically effective amount of a compound of formula (I):

Formula (I)

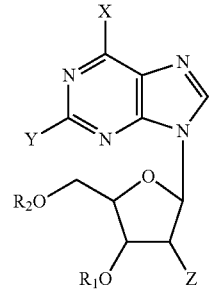

wherein

X and Y are the same or different and are hydrogen, halogen, $OR_3$, $SR_3$, $NR_3R_4$ or NHacyl;

Z is a halogen or $CF_3$.

$R_3$ and $R_4$ being the same or different and being hydrogen, a lower alkyl of 1 to 7 carbon atoms, an aralkyl compound selected from the group consisting of benzyl, benzyhydryl or methoxybenzyl, or an aryl compound selected from the group consisting of phenyl, chlorophenyl, toluoyl, methoxyphenyl and naphthyl;

NHacyl being alkanoyl or aroyl amide, alkanoyl being an alkyl carbonyl radical in which alkyl is a straight or branched chain saturated or unsaturated hydrocarbon radical having from 1 to 20 carbon atoms; and $R_1$ and $R_2$ are the same or different and are hydrogen, acyl or aroyl, acyl being an alkanoyl group of 1 to 20 carbon atoms and aroyl being benzoyl or naphthoyl; and salts, solvates, derivatives and prodrugs thereof. Another embodiment of the present disclosure is drawn to a method of conferring radiation sensitivity on a tumor cell comprising administering to said cell a compound of formula (I-a). In another embodiment, the tumor cells being sensitized to radiation are not any one or all of prostate, lung, or glioblastoma tumor cells.

Methods of synthesizing compounds of formula (I) are well known in the art and are disclosed in U.S. Pat. No. 4,751,221 to Watanabe et al. and is incorporated herein by reference in its entirety.

Another embodiment of the present disclosure is drawn to a method of potentiating radiotherapy treatment comprising administering to a patient in need thereof a therapeutically effective amount of a compound of formula (I-a):

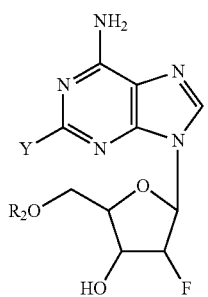

Formula (I-a)

wherein

Y is F, Cl, or Br;

$R_2$ is hydrogen or acyl; and salts, solvates, derivatives and prodrugs thereof. Another embodiment of the present disclosure is drawn to a method of conferring radiation sensitivity on a tumor cell comprising administering to said cell a compound of formula (I-a). In another embodiment, the tumor cells being sensitized to radiation are not any one or all of prostate, lung, or gioblastoma tumor cells.

Methods of synthesizing compounds of formula (I-a) are well known in the art and are disclosed in U.S. Pat. No. 6,949,640 to Montgomery et al. and U.S. Pat. No. 5,034,518 to Montgomery et al., both assigned to Southern Research Institute, the assignee of this application, and are both incorporated herein by reference in their entireties.

Another embodiment is drawn to methods for enhancing radiosensitivity of cell populations comprising exposing said cell populations to a sensitizing amount of a compound of the instant disclosure. Also provided herewith are methods for treating tumor growth comprising administering to a patient in need thereof a synergistic combination of radiation and a compound of the instant disclosure. All methods provided herein may also further comprise administering compounds of the instant disclosure concurrently with radiation throughout the course of treatment. For instance, compounds of the instant disclosure may be administered daily for a period before, after, or throughout the course of radiation therapy. In one embodiment, a compound of the instant disclosure is administered after directing radiotherapy but close enough in time to exhibit a combinatorial or synergistic effect. Likewise, a compound of the instant disclosure may be administering before directing radiotherapy but close enough in time to exhibit a combinatorial or synergistic effect. In one embodiment, the methods of the instant disclosure are not directed to any one or all of prostate, lung, or glioblastoma tumors.

While not limiting the scope of the disclosure, cancers treatable by the methods disclosed herein include, but are not limited to a colon cancer, a liver cancer, a colorectal cancer, a pancreatic cancer, a soft tissue cancers, a brain cancer, a head-and-neck cancer, a gastrointestinal cancer, a breast cancer, an ovarian cancer, a lymphoma, a sarcoma, a melanoma cancer of the cervix or endometrium, a bladder cancer, a renal cancer, or an ocular cancer.

Prodrug forms of the compounds bearing various nitrogen functions (amino, hydroxyamino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynl, cycloalkyl or cycloalkenyl groups as defined earlier.

(a) Carboxamides, —NHC(O)R
(b) Carbamates, —NHC(O)OR
(c) (Acyloxy)alkyl Carbamates, NHC(O)OROC(O)R
(d) Enamines, —NHCR(=CHCO$_2$R) or -NHCR(=CHCONR$_2$)
(e) Schiff Bases, —N=CR$_2$
(f) Mannich Bases (from carboximide compounds), RCONHCH$_2$NR$_2$ Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the invention.

Prodrug forms of carboxyl-bearing compounds of the invention include esters (—CO$_2$R) where the R group corresponds to any alcohol whose release in the body through enzymatic or hydrolytic processes would be at pharmaceutically acceptable levels. Another prodrug derived from a carboxylic acid form of the invention may be a quaternary salt type

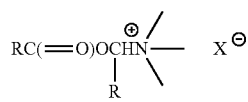

of structure described by Bodor et al., J. Med. Chem. 1980, 23, 469.

It is of course understood that the compounds of the present invention relate to all optical isomers and stereoisomers at the various possible atoms of the molecule.

Pharmaceutically acceptable salts of the compounds of the present invention include those derived from pharmaceutically acceptable inorganic or organic acids. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include alkali such as sodium and ammonia.

The compounds of the present invention can be synthesized by persons skilled in the art once aware of the present disclosure without undue experimentation. Procedures are available in the chemical literature suitable for preparing the requisite sugars or nucleosides. Along these lines, see Choi, Jong-Ryoo; Kim, Jeong-Min; Roh, Kee-Yoon; Cho, Dong-Gyu; Kim, Jae-Hong; Hwang, Jae-Taeg; Cho, Woo-Young; Jang, Hyun-Sook; Lee, Chang-Ho; Choi, Tae-Saeng; Kim, Chung-Mi; Kim, Yong-Zu; Kim, Tae-Kyun; Cho, Seung-Joo; Kim, Gyoung-Won PCT Int. Appl. (2002), 100 pp. WO 0257288 A1 20020725. Holy, Antonin; Votruba, Ivan; Tloustova, Eva; Masojidkova, Milena. Collection of Czechoslovak Chemical Communications (2001), 66(10), 1545-1592. Rejman, Dominik; Masojidkova, Milena; De Clercq, Eric; Rosenberg, Ivan Nucleosides, Nucleotides & Nucleic Acids (2001), 20(8), 1497-1522; Ubasawa, Masaru; Sekiya, Kouichi PCT Int. Appl. (2001), 39 pp WO 0164693 A1 20010907. Otmar, Miroslav; Masojfdkova, Milena; Votruba, Ivan; Holy, Antonin. Collection of Czechoslovak Chemical Communications (2001), 66(3), 500-506. Michal; Hocek, Michal; Holy, Antonin. Collection of Czechoslovak Chemical Communications (2000), 65(8), 1357-1373. Jeffery, A. L.; Kim, J.-H.; Wiemer, D. F. Tetrahedron (2000), 56(29), 5077-5083. Holy, Antonin; Guenter, Jaroslav; Dvorakova, Hana; Masojidkova, Milena; Andrei, Graciela; Snoeck, Robert; Balzarini, Jan; De Clercq, Erik. Journal of Medicinal Chemistry (1999), 42(12), 2064-2086. Janeba, Zlatko; Holy, Antonin; Masojidkova, Milena. Collection of Czechoslovak Chemical Communications (2001), 66(9), 1393-1406. Holy, Antonin; Guenter, Jaroslav; Dvorakova, Hana; Masojidkova, Milena; Andrei, Graciela; Snoeck, Robert; Balzarini, Jan; De Clercq, Erik. Journal of Medicinal Chemistry (1999), 42(12), 2064-2086. Dang, Qun; Erion, Mark D.; Reddy, M. Rami; Robinsion, Edward D.; Kasibhatla, Srinivas Rao; Reddy, K. Raja. PCT Int. Appl. (1998), 126 pp WO 9839344 A119980911. Arimilli, Murty N.; Cundy, Kenneth C.; Dougherty, Joseph P.; Kim, Choung U.; Oliyai, Reza; Stella, Valentino J. PCT Int. Appl. (1998), 74 pp WO 9804569. Sekiya, Kouichi; Takashima, Hideaki; Ueda, Naoko; Kamiya, Naohiro; Yuasa, Satoshi; Fujimura, Yoshiyuki; Ubasawa, Masaru Journal of Medicinal Chemistry (2002), 45(14), 3138-3142. Ubasawa, Masaru; Sekiya, Kouichi; Takashima, Hideaki; Ueda, Naoko; Yuasa, Satoshi; Kamiya, Naohiro. Eur. Pat. Appl. (1997), 56 pp EP 785208 A1 19970723. Hocek, Michal; Masojidkova, Milena; Holy, Antonin, Collection of Czechoslovak Chemical Communications (1997), 62(1), 136-146. Holy, Antonin; Votruba, Ivan; Tloustova, Eva; Masojidkova, Milena. Collection of Czechoslovak Chemical Communications (2001), 66(10), 1545-1592. Holy, Antonin; De Clercq, Erik Desire Alice. PCT Int. Appl. (1996), 57 pp. WO 9633200 A1 19961024. Rejman, Dominik; Rosenberg, Ivan. Collection of Czechoslovak Chemical Communications (1996), 61(Spec. Issue), S122-S123. Holy, Antonin; Dvorakova, Hana; Jindrich, Jindrich; Masojidkova, Milena; Budesinsky, Milos; Balzarini, Jan; Andrei, Graciella; De Clercq, Erik. Journal of Medicinal Chemistry (1996), 39(20), 4073-4088. Guanti, Giuseppe; Merlo, Valeria; Narisano, Enrica. Tetrahedron (1995), 51(35), 9737-46. Takashima, Hideaki; Inoue, Naoko; Ubasawa, Masaru; Sekiya, Kouichi; Yabuuchi, Shingo Eur. Pat. Appl. (1995), 88 pp. EP 632048 A1 19950104. Alexander, Petr; Holy, Antonin; Masojidkova, Milena, Collection of Czechoslovak Chemical Communications (1994), 59(8), 1853-69. Alexander, Petr; Holy, Antonin; Masojidkova, Milena; Collection of Czechoslovak Chemical Communications (1994), 59(8), 1853-69. Jindrich, Jindrich; Holy, Antonin; Dvorakova, Hana. Collection of Czechoslovak Chemical Communications (1993), 58(7), 1645-67. Holy, Antonin. Collection of Czechoslovak Chemical Communications (1993), 58(3), 649-74. Guanti, Giuseppe; Merlo, Valeria; Narisano, Enrica; Tetrahedron (1995), 51(35), 9737-46. Emishetti, Purushotham; Brodfuehrer, Paul R.; Howell, Henry G.; Sapino, Chester, Jr. PCT Int. Appl. (1992), 43 pp. WO 9202511 A1 19920220. Glazier, Arnold. PCT Int. Appl. (1991), 131 pp. WO 9119721. Kim, Choung Un; Luh, Bing Yu; Misco, Peter F.; Bronson, Joanne J.; Hitchcock, Michael J. M.; Ghazzouli, Ismail; Martin, John C Journal of Medicinal Chemistry (1990), 33(4), 1207-13. Rosenberg, Ivan; Holy, Antonin; Masojidkova, Milena. Collection of Czechoslovak Chemical Communications (1988), 53(11B), 2753-77. Rosenberg, Ivan; Holy, Antonin; Masojidkova, Milena. Collection of Czechoslovak Chemical Communications (1988), 53(11B), 2753-77.

While not being bound to any particular theory, it is believed that compounds of the instant disclosure, such as clofarabine, work synergistically with radiation therapy by sustaining the presence of DNA damage to increase the tumor response to radiation therapy. Clofarabine functions through the disruption of nucleotide metabolism by inhibiting DNA polymerases and ribonucleotide reductase (RnR), a class of enzymes necessary for recycling the nucleotide pool. RnR catalyzes the reduction of ribonucleotides into deoxyribonucleotides, providing the substrates for DNA synthesis and repair. Clofarabine is phosphorylated by cytosolic kinases (deoxycytidine kinase) to clofarabine 5'-monophosphate and by mono- and diphosphokinases to the active form, clofarbine 5'triphophate. Clofarabine 5'-triphosphate competes with deoxyadenosine triphosphate (dATP) for DNA polymerase-α and -ε and inhibits RnR by depleting deoxyribonucleotide triphosphate pools of deoxycytidine triphosphate and dATP. These actions culminate in the inhibition of DNA synthesis and both the induction of strand breaks and the inhibition of DNA repair. It is also possible that clofarabine can be incorporated into a repair patch, cause chain termination at the site of incorporation, prolong a DNA damage response signal, and produce more permanent DNA damage initiated by radiation therapy.

The following examples illustrate and describe aspects of the present disclosure. The examples show and describe only limited embodiments but it is to be understood that the disclosure is capable of use in various other combinations, modifications, and environments and is capable of changes or modifications within the scope of the concept as expressed herein, commensurate with the teachings and/or the skill or knowledge of the relevant art. The procedures described in the following examples are also disclosed in Cariveau et al., *Clofarabine Acts as Radiosensitizer In Vitro and In Vivo by Interfereing with DNA Damage Response*, INT. J. RADIATION ONCOLOGY BIOL. PHYS., 70(1): 213-220 (2008), which is incorporated herein by reference in its entirety.

EXAMPLE 1

Chemotherapeutic Preparation

A chemotherapeutic agent such as clofarabine (2-chloro-9-(2-deoxy-fluoro-β-D-arabino-furanosyl)-adenine) (Genzyme), gemcitabine (Elli Lilly), or 5-FU (American Pharmaceutical Partners) is dissolved in DMSO (dimethylsulfoxide) to a stock concentration of 100 mM and stored at −20° C. The compounds are reconstituted, to working dilutions, in DMEM (Dulbecco's Modified Eagle's Medium) culture medium containing fetal bovine serum, L-glutamine (2 mM), and 1% penicillin-streptomycin immediately before use.

EXAMPLE 2

Radiation

For irradiations, an X-RAD 320 Irradiation Cabinet (Precision X-ray, East Haven, Conn.) is employed at 320 KV and 160 mA, with a 0.8 mm Sn+0.25 mm Cu+1.5 mm Al (HVL≅3.7 Cu) filter at a TSD of 20 cm and a dose rate of 3.4 Gy/min. All irradiations are conducted under normal atmospheric pressure and temperature.

EXAMPLE 3

γ-H2AX Focus Formation Assay

HeLa and DLD-1 (HCT15) (from ATCC, CCL-2, Manassas Va.) cells are maintained in exponential growth in DMEM (Dulbecco's Modified Eagle's Medium)-10% FBS (Fetal bovine serum), in a 5% $CO_2$ humidified atmosphere. Exponentially growing cultures of HeLa cells are plated on sterile, 22 cm coverslips in DMEM (Dulbecco's Modified Eagle's Medium)-10% FBS (Fetal bovine serum), and incubated for 24 hours at 37° C. in 5% $CO_2$ humidified air. Cells are treated with 0, 5, 10 100, or 1000 nM clofarabine, mock or irradiated with 6 Gy, and harvested 30 minutes later. For time course studies of γ-H2AX foci presence, cells are treated with 0, 5, or 10 nM clofarabine, mock or irradiated with 6 Gy, and harvested at 0, 0.5, 2, 8, and 24 hrs. Immunofluorescence is used to determine the effects of Clofarabine on the induction and maintenance of γ-H2AX foci. The number of foci per nucleus are then counted from a population of at least 25 cells, and graphed as the mean and standard deviation.

Figure 2:
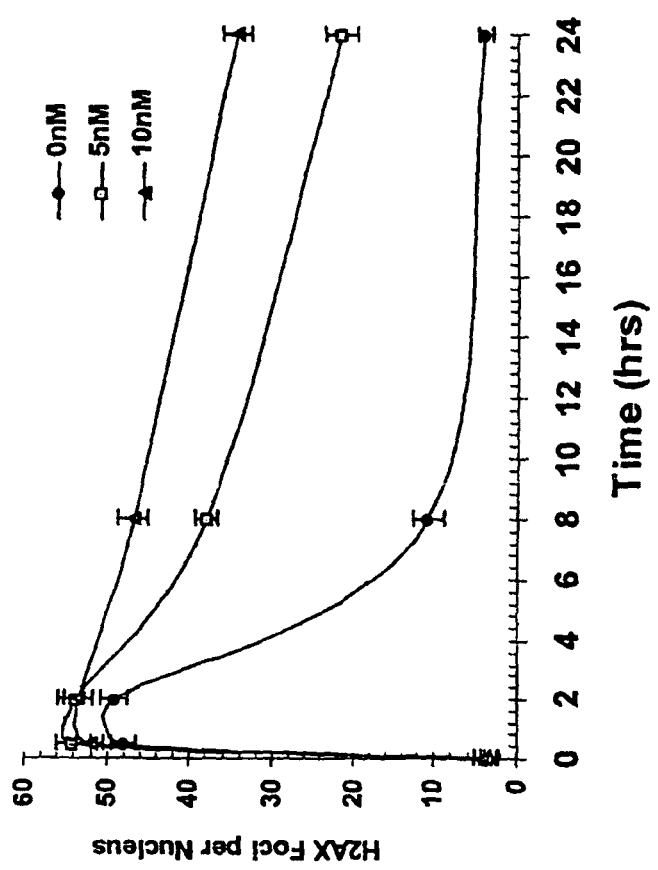
FIG. 2 is a graph showing the mean γ-H2AX nuclear foci per nucleus for irradiated cells treated with different concentrations of clofarabine.

The assay described above was implemented and results are shown in FIG. 1, which demonstrates that clofarabine prolongs the existence of IR-induced γ-H2AX foci. HeLa cells were treated with clofarabine for one hour, irradiated with 0 (Mock) or 6 Gy (IR), and then harvested. Immunofluorescence microscopy was employed to detect radiation-induced γ-H2AX foci. FIG. 2 shows that clofarabine prolongs the existence of IR-induced γ-H2AX foci. The mean γ-H2AX nuclear foci per nucleus was determined for each image using Image Pro 5.1. Error bars represent+/−1 SD of the mean of three independent experiments.

EXAMPLE 4

Radiosensitivity Assays

Figure 3:
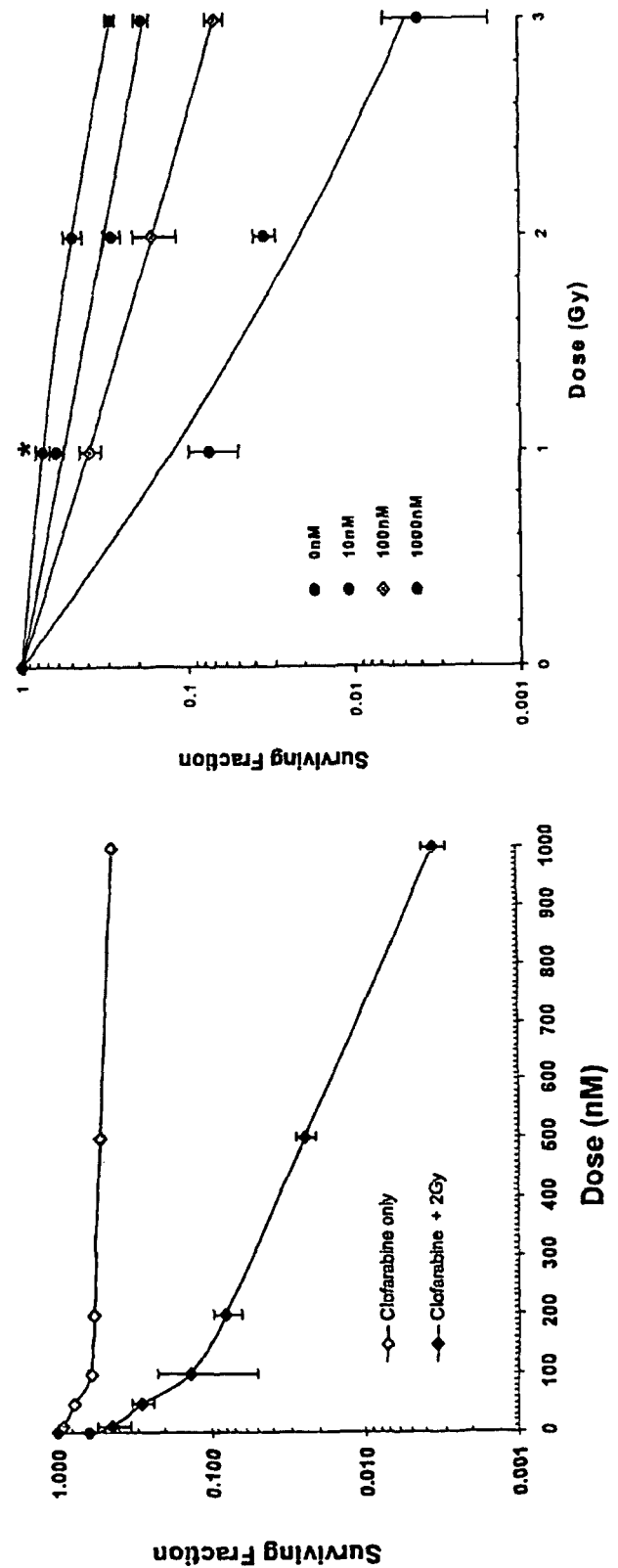
FIG. 3 shows survival curves for fractions of cells treated with clofarabine only and for fractions of cells treated with both clofarabine and irradiation.

To determine clofarabine's radiosensitizing effect, a colony-forming assay using a series of clofarabine doses (0-1,000 nM) with and without 2-Gy radiation is performed. HeLa cells are incubated with clofarabine for 4 h before radiation therapy. Clofarabine's radiosensitivity was tested and the results presented in FIG. 3, which shows that clofarabine increases cellular radiosensitivity. HeLa cells were seeded at limiting dilutions and treated with clofarabine for 4 hours prior to irradiation, continuously exposed to the drug for additional 20 hours, harvested 10-12 days later and stained with crystal violet. The survival curves with each data point representing the mean of three independent experiments are shown with the error bars representing+/−1 SEM.

EXAMPLE 5

Comparison of Clofarabine, Gemcitabine, and 5-FU-induced Radiosensitization

Figure 4:
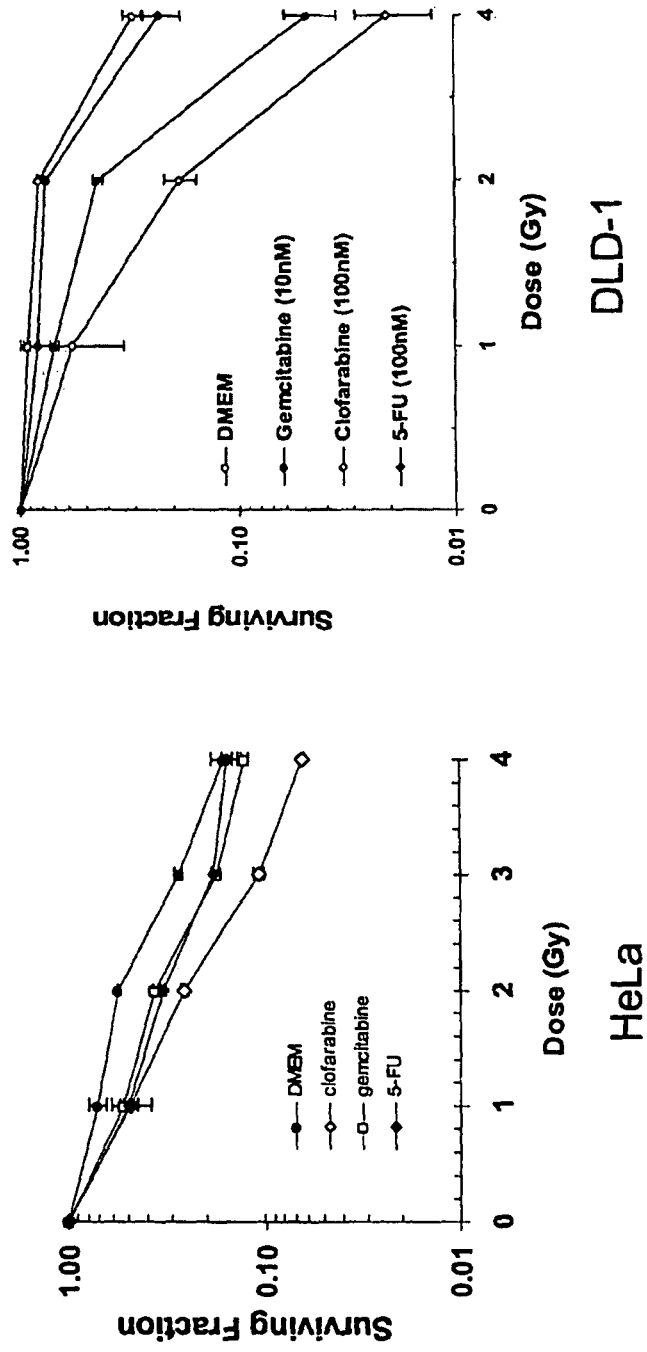
FIG. 4 presents graphs comparing the radiosensitization activity of clofarabine, gemcitabine, and fluorouracil ("5-FU").

To compare clofarabine's radiosensitizing potential with other proven radiosensitizing anti-metabolites, radiosensitivity is tested in HeLa cells treated with a combination of clofarabine, gemcitabine, or 5-FU with radiation therapy. The agents are administered at the same doses and schedule to identify the median lethal dose ($LD_{50}$) for each drug. The $LD_{50}$ is then used for each agent in subsequent experiments. Clofarabine, gemcitabine and 5-FU were tested and the results are presented in FIG. 4. Cells were seeded at limiting dilutions and treated with clofarabine, gemcitabine or 5-FU for 4 hours prior to irradiation, continuously exposed to the drug for additional 20 hours, harvested 10-12 days later and stained with crystal violet. Error bars represent+/−1 SEM, graphed are the mean of three independent experiments.

EXAMPLE 6

Cytotoxicity, Radiosensitivity, and Chemo-Radiation Synergism

HeLa or DLD-1 cells are plated at limiting dilutions in 6-well plates and incubated for 24 hrs at 37° C. in a 5% $CO_2$-humidified environment. For cytotoxicity assays, cells are then treated with doses of clofarabine, gemcitabine or 5-FU for four hours and fresh media added 20 hrs later.

For radiation sensitivity, cells are treated with clofarabine, gemcitabine, or 5-FU, mock, or irradiated with 2Gy alone, or 1-4Gy, and media changed 20 hr later. Cultures are then incubated for 10-12 days, harvested and stained with 0.5% crystal violet in methanol. Colony numbers are determined with a dissecting microscope. A population of >50 cells are counted as one colony, and the number of colonies are expressed as a percentage of the value for untreated controls and those treated with clofarabine, gemcitabine or 5-FU. The survival curves are plotted by linear regression analyses, and the $D_0$ value represents the radiation dose that leads to 37% survival. Sensitizing enhancement ratios (SER) were then calculated according to the $D_0$ values using the following formula:

$$SER = \frac{D_0 \text{ untreated cells}}{D_0 \text{ treated cells}}$$

The combination index (CI) is then used to determine whether the interaction is synergistic. The combination index (CI) is described in Pauwels et al., F. *Cell Cycle Effect of Gemcitabine and its Role in the Radiosensitizing Mechanism in Vitro.*, INT. J. RADIAT. ONCOL. BIOL. PHYS., 57:1075-1083 (2003) and Giovannetti et al., *Synergistic Cytotoxicity and Pharmacogenetics of Gemcitabine and Pemetrexed Combination in Pancreatic Cancer Cell Lines*, CLIN. CANCER RES., 10:2936-2943 (2004), which are incorporated herein by reference in their entirety. To determine whether the interaction is synergistic (CI≤0.7), additive (0.7≤CI≤0.9), or antagonistic (0.9≤CI≤1.1), the following calculations are employed:

$$CI = \frac{(D)_1}{(D_x)_1} + \frac{(D)_2}{(D_x)_2}$$

where $(D)_1$ is the median lethal does (lethal for 50% of test subjects) ($LD_{50}$) in nanomoles for combination treatment of clofarabine with IR, $(D)_2$ is the $LD_{50}$ in Gy for combination treatment of clofarabine with radiation therapy, $(D)_2$ is the $LD_{50}$ in Gray for combination treatment of clofarabine with radiation therapy, and $(D_x)_1$ and $(D_x)_2$ are the $LD_{50}$ of clofarabine and radiation therapy alone. Sensitizer enhancement ratios (SER) for clofarabine, gemcitabine or 5-FU are calculated based on the surviving fraction at 2 Gy. Each experiment is repeated at least twice and statistical significance (at p<0.05) established using Student's t-test.

Figure 7:
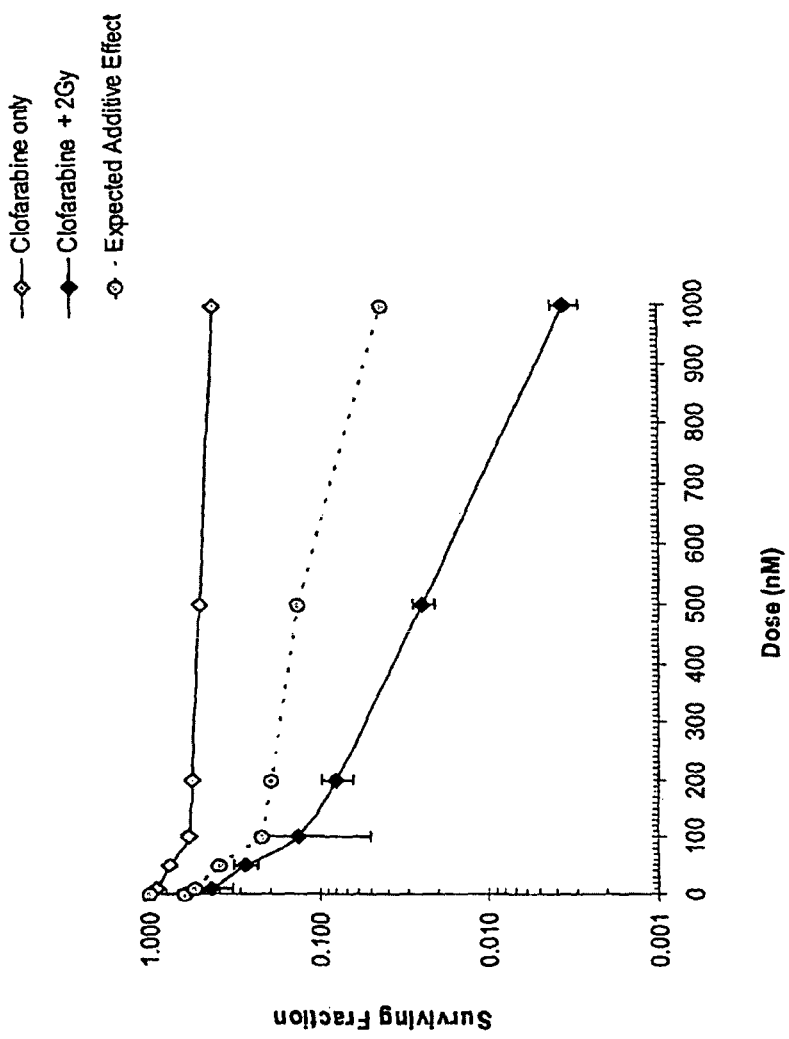
FIG. 7 shows the synergistic effect of radiation and clofarabine used in conjunction with each other and compares results to the expected additive effect.

The methods described above were implemented and the results shown in FIG. 7. FIG. 7 shows the synergistic effect of radiation and clofarabine when used together and compares results to the expected additive effect based on the method described above.

EXAMPLE 7

Colon Cancer Xenograft Assay

DLD-1 human colon tumors are implanted s.c. in male athymic nu/nu mice near the right flank. Tumors are allowed to reach 100-256 mg in weight (100-256 mm in size) before the start of treatment. A sufficient number of mice are implanted so that tumors in a weight range as narrow as possible are selected for the trial on the day of treatment initiation (day 14 after tumor implantation). Two separate studies are conducted. In the first set of experiments, mice are treated with clofarabine alone or clofarabine plus radiation at 3 Gy per treatment for a total dose of 18 Gy. In the second set of experiments, mice are treated with clofarabine, gemcitabine or 5-FU via i.p. injection or the drugs plus radiation at 3 Gy per treatment for a total dose of 9 Gy. Tumor volume and size are recorded on a daily basis, and are not allowed to rupture or ulcerate the skin.

Figure 5:
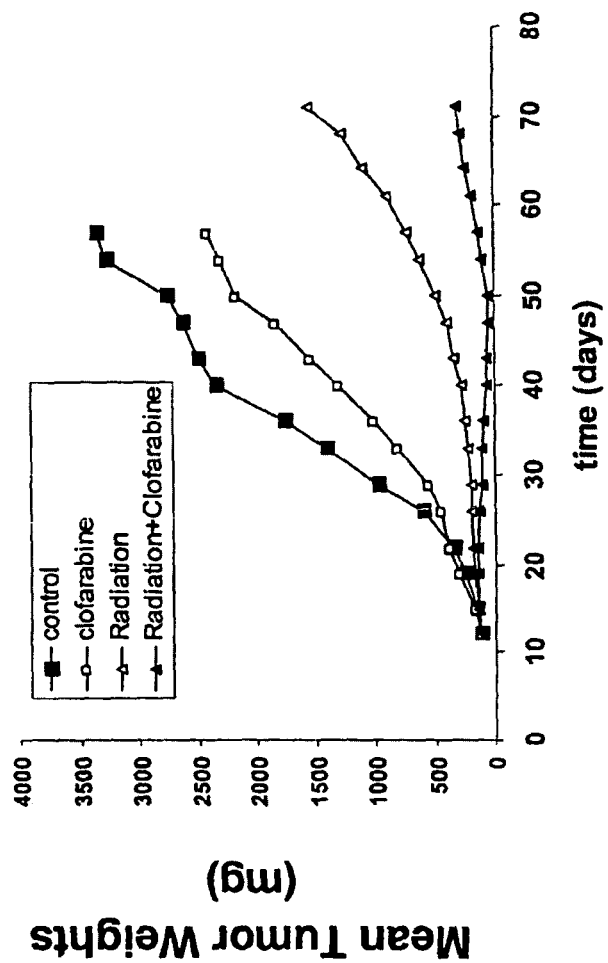
FIG. 5 graphically illustrates the mean change in tumor weight for in vivo tumors treated with clofarabine alone, radiation alone, and a combination of radiation and clofarabine.
Figure 6:
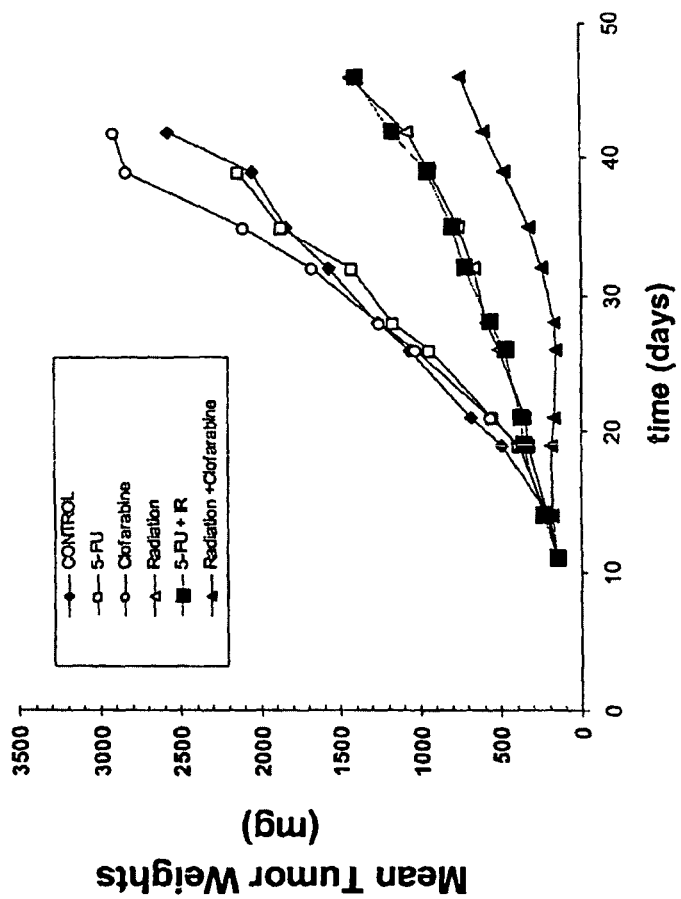
FIG. 6 graphically illustrates the mean change in tumor weight for in vivo tumors treated with 5-FU alone, clofarabine alone, radiation alone, a combination of radiation and 5-FU, and a combination of radiation and clofarabine.

The assay described above was performed and the results are provided in FIGS. 5 and 6. FIG. 5 shows that clofarabine sensitizes tumors to radiation in vivo. DLD-1 human colon tumor were implanted s.c. in male athymic mice. Mice were treated with clofarabine alone or clofarabine plus radiation. FIG. 6 also shows clofarabine's sensitizing effects on tumors in vivo. Mice were treated with clofarabine, gemcitabine or 5-FU via i.p. injection or the drugs plus radiation. Tumor volume and size were recorded on a daily basis. Shown are the mean tumor weights of each group as a function of time after implantation.

EXAMPLE 8

Head and Neck, Pancreatic, and Colon Cancer Xenograph Assays

Xenograph models including DU-145 (prostate), NCI-H460 NSCL (lung), SF-295 CNS (glioblastoma), SR475HN (head and neck), PANC-1 (pancreatic), and HCT-116 (colon) are employed to study the effect of compounds according to the instant disclosure combined with radiation therapy. Mice are implanted with tumor fragments subcutaneously from an in vivo passage and the tumors are allowed to grow. Mice with tumors in a designated size range are selected for the studies. The NCI-H460 and SF-295 studies use 12 Gy total radiation delivered in four, 3 Gy fractions every three days combined with clofarabine injected by intraperitoneal (ip) injection daily for 10 days at a dosage of 30 mg/kg/injection. The remaining tumor models are given 20 Gy, in 2 Gy fractions daily for five days for two weeks combined with clofarabine injected ip daily for 12 days at a dosage of 30 mg/kg/injection.

The methods described above were employed and the resulting data is presented in Table 1 below.

TABLE 1

Results for Combination of Clofarabine and Radiation In Vivo Studies

| Tumor | Agent | Treatment | Growth Delay (T-C, days) | Tumor-Free Survivors/ Total |
|---|---|---|---|---|
| DU-145 | Clofarabine | 30 mg/kg/dose, ip, d. 13-24 | 4.3 | 0/6 |
| prostate | Radiation | 2 Gy, d. 13-17, 20-24 | 18.3 | 0/6 |
|  | Combination* |  | 19.8 | 0/6 |
| NCI-H460 | Clofarabine | 30 mg/kg/dose, ip, d. 8-17 | 4.6 | 0/6 |
| NSCL | Radiation | 3 Gy, d. 8, 11, 14, 17 | 9.4 | 0/6 |
| (lung) | Combination* |  | 16.9 | 0/6 |
| SF-295 CNS | Clofarabine | 30 mg/kg/dose, ip, d. 8-17 | -0.8 | 0/6 |
| (glioblastoma) | Radiation | 3 Gy, d. 8, 11, 14, 17 | 7.2 | 0/6 |
|  | Combination* |  | 9.5 | 0/6 |
| SR475 | Clofarabine | 30 mg/kg/dose, ip, d. 19-30 | 18.2 | 0/6 |
| (head & neck) | Radiation | 2 Gy, d. 19-23, 26-30 | 73.2 | 0/6 |
|  | Combination* |  | >162.0 | 4/6 |
| PANC-1 | Clofarabine | 30 mg/kg/dose, ip, d. 12-23 | 17.2 | 0/6 |
| (pancreatic) | Radiation | 2 Gy, d. 12-16, 19-23 | 1.7 | 0/6 |
|  | Combination* |  | 63.8 | 0/6 |
| HCT-116 | Clofarabine | 30mg/kg/dose, ip, d. 13-24 | 24.2 | 0/6 |
| (colon) | Radiation | 2 Gy, d. 13-17, 20-24 | 29.3 | 0/6 |
|  | Combination* |  | >78.9 | 5/6 |

*Clofarabine was given first followed by radiation 1 hour later.

SR475HN head and neck tumors were radiosensitized by clofarabine with T-C values (based on 2 tumor doublings) of 18.2, 73.2, and >162 days for clofarabine, radiation, and the combination, respectively. PANC-1 pancreatic tumors were radiosensitized by clofarabine with T-C values (based on 2 tumor doublings) of 17.2, 1.7, and 63.8 days for clofarabine, radiation, and the combination, respectively. HCT-116 colon tumors were radiosensitized by clofarabine with T-C values (based on 3 tumor doublings) of 24.2, 29.3, and >78.9 days for clofarabine, radiation, and the combination, respectively. The radiosensitizing capacity of gemcitabine tracked with the clofarabine results. Clofarabine had no effect on the growth of SF-295 glioblastoma which was not enhanced by radiation. There was no difference between radiation alone and radiation combined with clofarabine in DU-145 prostate xenografts. The combined effect on NCI-H460 lung tumors appeared to be additive with T-C values (based on time to 3 tumor doublings) of 4.6, 9.4, and 16.9 days for clofarabine, radiation, and the combination, respectively. Three out of the six tumor models tested showed marked radiosensitization with clofarabine while another tumor model showed an additive effect. Two out of the six models tested showed no evidence of an interaction between clofarabine and radiation. The data indicates a trend showing clofarabine's ability to radiosensitize tumor cells.

EXAMPLE 9

Anti-Tumor Activity of Clofarabine in Cisplatin-Resistant Ovarian Cancer Cells

The cytoxicity of a compound of the instant disclosure against two ovarian cell lines, SKOV-3 and IGROV-1 is tested. A standard clonogenic survival assay is performed such as that described in Munshi et al., *Clonogenic Cell Survival Assay*, METHODS MOL. MED., 110-21-8 (2005), which is incorporated herein by reference in its entirety. Clofarabine, as well as cisplatin (used as a comparison control), is added to the cells at indicated doses for 24 hours before they are removed.

Figure 8:
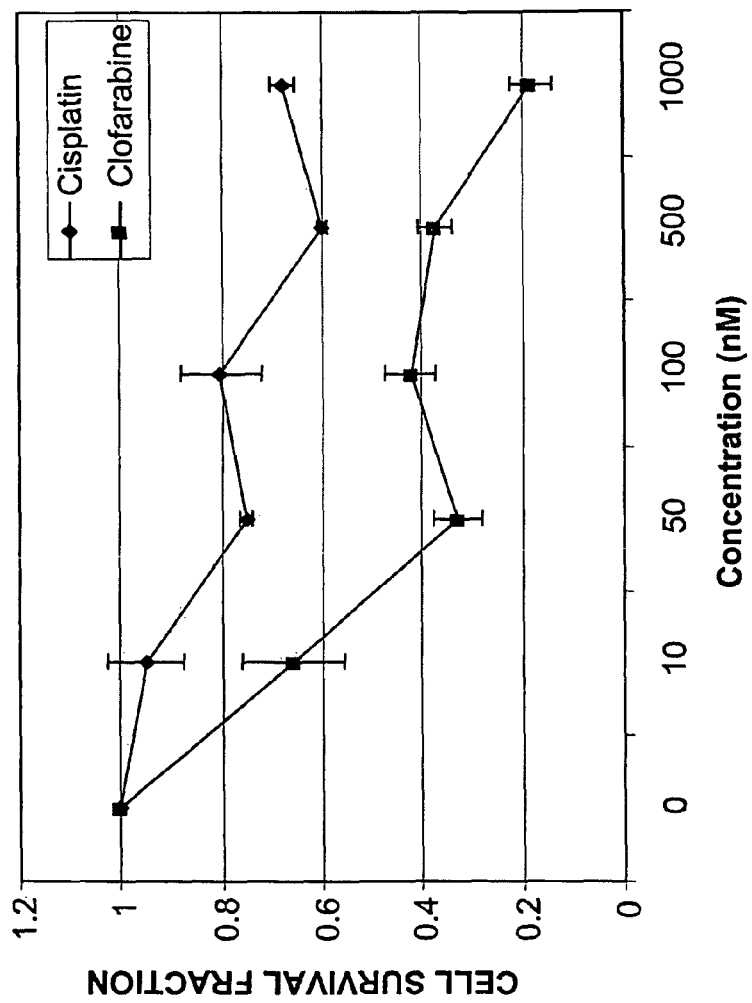
FIG. 8 shows the antitumor effect of clofarabine on SKOV-3 cells.
Figure 9:
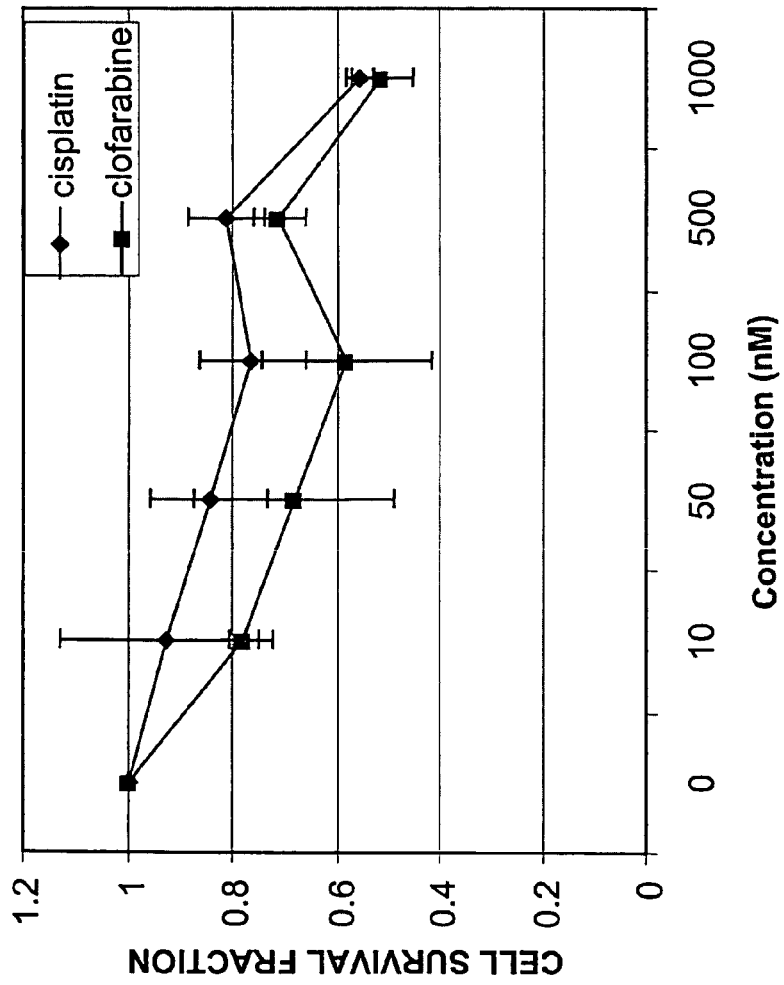
FIG. 9 shows the antitumor effect of clofarabine on IGROV-1 cells.

The procedure described above was employed and the results are presented in FIGS. 8 and 9. As seen in FIG. 8, in SKOV-3 cells, which is considered a cisplatin-resistant cell line, clofarabine shows significant tumor cell killing compared with cisplatin. FIG. 9 shows that clofarabine also shows increased activity in IGROV-1 cells compared with cisplatin.

Formulations

The compounds of the present disclosure can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art (5, 6). See Banker and Chalmers PHARMACEUTICS AND PHARMACY PRACTICE, 238-250 (J.B. Lippincott Co., Philadelphia, Pa. Eds. 1982) and Toissel, ASHP HANDBOOK ON INJECTABLE DRUGS, 622-630 (4th ed. 1986), which are incorporated herein by reference in its entirety.

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present disclosure should be sufficient to affect a therapeutic response in the animal over a reasonable time frame. One skilled in the art will recognize that dosage will depend upon a variety of factors including a condition of the animal, the body weight of the animal, as well as the severity and stage of the condition being treated.

A suitable dose is that which will result in a concentration of the active agent in a patient which is known to affect the desired response. The preferred dosage is the amount which results in maximum inhibition of the condition being treated, without unmanageable side effects.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present disclosure can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present disclosure can be administered in the form of nose drops, or metered dose and a nasal or buccal inhaler. The drug is delivered from a nasal solution as a fine mist or from a powder as an aerosol.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicates to be incorporated by reference.

The invention claimed is:

1. A method for treating a head-and-neck tumor, a pancreatic tumor, or a colon tumor comprising administering to a patient in need thereof a synergistic combination of ionizing radiation and clofarabine, and inhibiting or delaying the growth of the head-and-neck tumor, the pancreatic tumor, or the colon tumor.

2. The method according to claim 1 wherein the clofarabine is administered to the patient after subjecting the patient to radiotherapy.

3. The method according to claim 1, wherein the clofarabine is administered to the patient before subjecting the patient to radiotherapy.

4. The method according to claim 1, wherein the clofarabine is administered to the patient in daily doses.

5. The method according to claim 1, wherein the tumor is a head-and-neck tumor.

6. The method according to claim 1, wherein the tumor is a pancreatic tumor.

7. The method according to claim 1, wherein the tumor is a colon tumor.

* * * * *